US00PP34733P2

(12) United States Plant Patent
de Groot

(10) Patent No.: US PP34,733 P2
(45) Date of Patent: Nov. 15, 2022

(54) GROUNDCOVER ROSE PLANT NAMED 'BORUIWHIVA'

(50) Latin Name: *Rosa hybrida*
Varietal Denomination: BORUIWHIVA

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 17/841,399

(22) Filed: Jun. 15, 2022

(51) Int. Cl.
*A01H 5/02* (2018.01)
*A01H 6/74* (2018.01)

(52) U.S. Cl.
USPC ..... Plt./101

(58) Field of Classification Search
USPC ..... Plt./101, 102
See application file for complete search history.

*Primary Examiner* — Susan McCormick Ewoldt
(74) *Attorney, Agent, or Firm* — Cassandra Bright

(57) ABSTRACT

A new and distinct groundcover *Rosa* plant named 'BORUIWHIVA' is disclosed, characterized by abundant highly scented white flowers flushed pink. Plants are compact and low growing, suitable for groundcover use. The new variety is a *Rosa*, normally produced as an outdoor garden or container plant.

1 Drawing Sheet

Latin name of the genus and species: *Rosa hybrida.*
Variety denomination: 'BORUIWHIVA'.

BACKGROUND OF THE INVENTION

The new *Rosa* cultivar is a product of a planned breeding program conducted by the inventor. The cross resulting in this new variety was made in April of 2009 at a nursery in Boskoop, The Netherlands.

The seed parent is the unpatented variety *Rosa* 'Snow Pavement'. The pollen parent is the unpatented variety *Rosa* 'BOKRATRACK'. The new variety was selected in September 2012 by the inventor at the same nursery in Boskoop, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, The Netherlands, in September 2012, and has shown that the unique features of this cultivar are stable and reproduced true to type in successive generations.

SUMMARY OF THE INVENTION

The cultivar 'BORUIWHIVA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BORUIWHIVA' These characteristics in combination distinguish 'BORUIWHIVA' as a new and distinct *Rosa* cultivar:

1. Groundcover shrub rose.
2. Abundant white to very light pink flowers.

3. Few hips produced.
4. Strong rose fragrance.

PARENTAL COMPARISON

Plants of the new cultivar 'BORUIWHIVA' are similar to plants of the seed parent in most horticultural characteristics, however, plants of the new cultivar 'BORUIWHIVA' differ in the following:

1. Flowers of the new cultivar have more pink coloration than flowers of the seed parent.
2. Plants of the new cultivar are more compact than plants of the seed parent.
3. Plants of the new cultivar produce less thorns than plants of the seed parent.

Plants of the new cultivar 'BORUIWHIVA' are similar to plants of the pollen parent in most horticultural characteristics, however, plants of the new cultivar 'BORUIWHIVA' differs in the following;

1. Foliage of the new cultivar is lighter green than foliage of the pollen parent.
2. The new cultivar produces more flowers than plants of the pollen parent.
3. Plants of the new cultivar are more compact than plants of the pollen parent.

COMMERCIAL COMPARISON

Plants of the new cultivar 'BORUIWHIVA' can be compared to the commercial cultivar *Rosa* 'Blanc double de Coubert', unpatented. These cultivars are similar in most horticultural characteristics, however 'BORUIWHIVA' differs in the following:

1. This new cultivar has flowers with more pink coloration than this comparator.
2. This new cultivar produces more branches per plant than this comparator.
3. The new cultivar is easier to propagate than this comparator.

4. The new cultivar is more suited as a groundcover than plants of this comparator.

Plants of the new cultivar 'BORUIWHIVA' can be compared to the commercial cultivar *Rosa* 'Mont Blanc', unpatented. These cultivars are similar in most horticultural characteristics, however 'BORUIWHIVA' differs in the following:

1. This new cultivar has flowers with more pink coloration than this comparator.
2. This new cultivar produces more flowers per plant than this comparator.
3. The new cultivar has less thorns than this comparator.

BRIEF DESCRIPTION OF THE PHOTOGRAPH

The accompanying photograph illustrates a close-up view of a typical flower of 'BORUIWHIVA'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BORUIWHIVA' plants grown outdoors in Camarillo, Calif. The growing temperature ranged from approximately 15° C. to 28° C. during the day and from approximately 8° C. to 15° C. during the night. Measurements were taken in April and May. General light conditions were very bright, normal sunlight. Measurements and numerical values represent averages of typical plant types.

Botanical classification: *Rosa* 'BORUIWHIVA'.

Market classification: Groundcover shrub rose.

PROPAGATION

Time to initiate roots: 10 days at approximately 25° C.

Time to produce a rooted cutting: 21 days at approximately 25° C.

PLANT

Growth habit: Dense, low growing, groundcover type.

Age of plant described: 1 year.

In a container size: 2 gallon.

Height: 45 cm.

Plant spread: 70 cm.

Branching Characteristics:

Length of primary lateral branches: Approximately 12 cm to 18 cm.

Diameter of lateral branches: Approximately 9 mm.

Quantity of lateral branches: 12 to 20 within 6 weeks of emerging from dormancy.

Branching arrangement: Dense, compound.

Branches-young wood:

*Diameter*.—Approximately 4 mm.

*Texture*.—Smooth.

*Approximately density/quantity of thorns*.—Approximately 1 per 1.5 linear cm.

*Color*.—Near RHS Yellow-Green N144C.

Branches-old wood:

*Diameter*.—Approximately 6 mm.

*Color*.—Near RHS Greyed-Purple 183A flushed Grey-Brown 199B.

*Texture*.—Smooth with a very few striations.

*Internode*.—4 to 6 cm.

Thorns:

*Shape*.—Needlelike.

*Color*.—Near RHS Grey-Brown 199B.

*Length*.—5 mm.

*Diameter*.—3 mm at base, 1 mm along 90% of length.

FOLIAGE

Leaf:

*Arrangement*.—Imparipinnate.

*Quantity*.—Approximately 7 to 10 per main branch.

*Average length*.—Approximately 10.5 cm.

*Average width*.—Approximately 5.4 cm.

Leaflet:

*Quantity*.—Most commonly 7 per leaf. Rarely 3 or 5.

*Average length*.—Approximately 3.5 cm.

*Average width*.—Approximately 1.5 cm.

*Shape of blade*.—Elliptic.

*Apex*.—Acute.

*Base*.—Broad tapered.

*Margin*.—Very finely serrate.

*Texture of top surface*.—Smooth.

*Texture of bottom surface*.—Smooth.

*Pubescence*.—None observed.

*Leaf internode length*.—2.5 cm to 3 cm.

*Color*.—Young foliage upper side: Near RHS Green 137C flushed Yellow-Green 144A. Young foliage under side: Near RHS Green 138B. Mature foliage upper side: Near RHS Green 137A. Mature foliage under side: Near RHS Green 137B.

*Venation*.—Type: Pinnate. Venation color upper side: Near Green 143C. Venation color under side: Near Green 138B.

Stipule:

*Length*.—1.5 cm.

*Width*.—4 mm.

*Color*.—Near RHS Green 143B.

*Texture*.—Smooth.

Petiole:

*Length*.—2.7 cm.

*Width*.—2 mm.

*Color*.—Near RHS Green 143B.

*Texture*.—Glabrous.

Rachis:

*Length*.—4 cm.

*Width*.—1.5 mm.

*Color*.—Near RHS Green 143B.

*Texture*.—Glabrous.

FLOWER

Natural flowering season: April through October in Southern California.

Begins flowering after how many years/months: 2 months.

Inflorescence type: Multiflora.

Rate of flower opening: Approximately 3 days from bud to fully opened flower.

Flower longevity on plant: 3 to 4 days, after fully opened.

Quantity of flowers: Most commonly 3 flowers per flowering axil.

Inflorescence size:
*Diameter*.—Approximately 12 cm.
*Height*.—Approximately 6 cm.
Flower size:
*Diameter*.—Approximately 6.0.
*Height*.—Approximately 3.0 cm.
Peduncle:
*Length*.—3.5 cm.
*Diameter*.—3 mm.
*Color*.—Near RHS Yellow-Green 144B.
*Texture*.—Glabrous.
Petals:
*Petal arrangement*.—Loose radial.
*Length*.—3.5 cm.
*Width*.—3.0 cm.
*Shape*.—Obcordate.
*Margin*.—Entire, slightly undulate.
*Apex*.—Retuse.
*Base*.—Cuneate.
*Petal quantity*.—20 to 30.
*Texture*.—Glabrous all surfaces.
*Color*.—When opening: Upper surface: Near RHS Red-Purple 69D, lightly flushed Purple 75C. Apex flushed Red-Purple N74D. Lower surface: Near RHS Red-Purple 69D, lightly flushed Purple 75C. Apex flushed Red-Purple N74D. Fully opened: Upper surface: Near RHS White N155B flushed Red-Purple 69C. apex flushed 69B. Lower surface: Near RHS White N155B flushed Red-Purple 69C. apex flushed 69B.
Bud:
*Shape*.—Ovate.
*Length*.—Approximately 2.0 cm.
*Diameter*.—Approximately 1.1 cm.
*Color*.—Near RHS Red-Purple 62C, base 62D.
Sepals:
*Quantity*.—5.
*Length*.—2.8 cm to 3.1 cm.
*Width*.—7 mm at base.
*Shape*.—Very narrow deltoid.
*Color*.—Interior Surface: Near Green 138C. Exterior Surface: Near Green 138B.
*Texture*.—Smooth.
Receptacle:
*Length*.—1 cm.
*Width*.—1 cm.
*Shape*.—Spherical.
*Color*.—Near Green 137D.
Fragrance: Strong, sweet rose scent.

REPRODUCTIVE ORGANS

Stamens:
*Quantity*.—Average 70.
*Filament length*.—Average 7 mm.
*Filament color*.—White 155C.
Anthers:
*Length*.—2 mm.
*Shape*.—Oblong.
*Color*.—RHS Yellow-Orange 22A.
*Pollen*.—Scant, colored near Yellow-Orange 22A.
Pistil:
*Number*.—Indistinguishable, fused into a single conglomerate structure.
*Length*.—6 mm.
*Style*.—Length: Approximately 4 mm. Color: Near RHS White 155C.
Stigma:
*Shape*.—Orbicular.
*Color*.—RHS White 155C.

OTHER CHARACTERISTICS

Disease/pest resistance: As typical of *Rosa rugosa*, the new variety is not prone to typical mildew diseases of roses in damp conditions. Neither resistance nor susceptibility to normal diseases and pests of garden roses has been observed.
Temperature tolerance: USDA Zones 3-9.
Drought tolerance: Some tolerance when established.

What is claimed is:

1. A new and distinct Groundcover Rose plant named 'BORUIWHIVA' as herein illustrated and described.

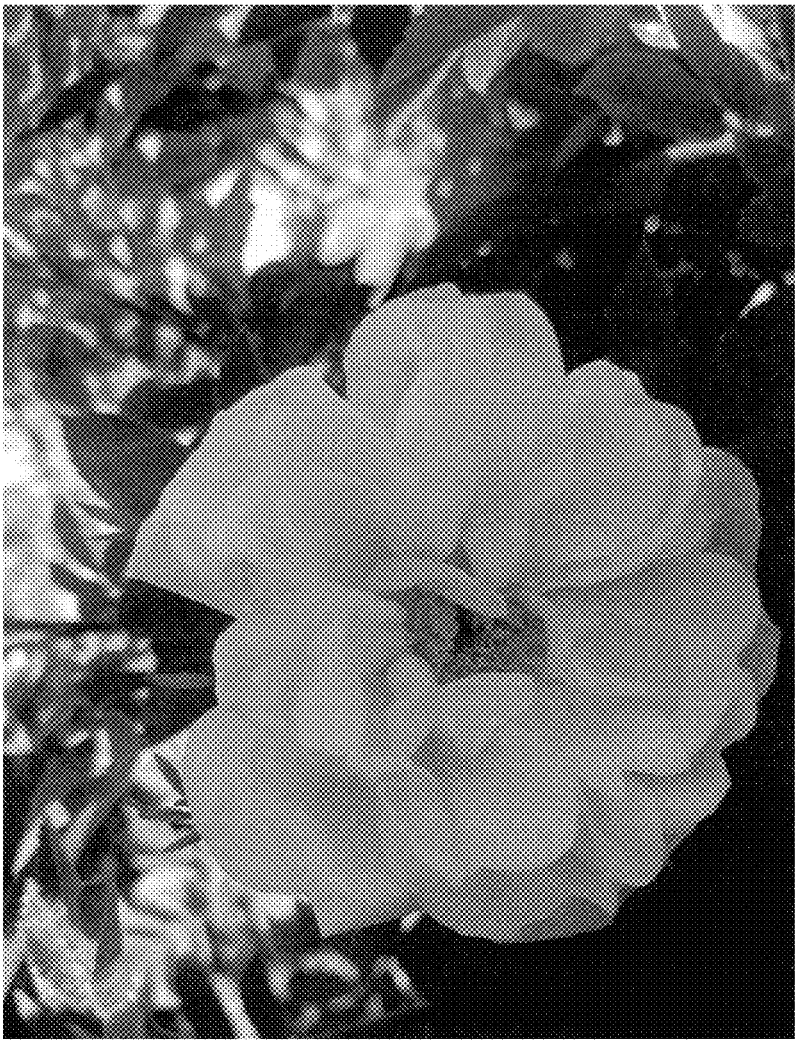

* * * * *